United States Patent [19]
Lee

[11] Patent Number: 5,250,046
[45] Date of Patent: Oct. 5, 1993

[54] HEATED FORCEPS

[76] Inventor: Curtis O. Lee, 3416 Riverwoods Dr., Rockford, Mich. 49341

[21] Appl. No.: 858,098

[22] Filed: Mar. 26, 1992

[51] Int. Cl.$^5$ ............................................. A61B 17/50
[52] U.S. Cl. ....................................... 606/29; 606/52; 606/42; 606/211
[58] Field of Search ................................ 606/27-31, 606/41, 42, 51, 52, 205, 210, 211; 219/229, 230, 237

[56] References Cited

U.S. PATENT DOCUMENTS

| | | | |
|---|---|---|---|
| 728,883 | 5/1903 | Downes | 606/28 |
| 1,009,008 | 11/1911 | Asch | 219/230 X |
| 3,100,489 | 8/1963 | Bagley | 606/42 |
| 3,980,861 | 9/1976 | Fukunaga | 606/28 X |
| 4,213,460 | 7/1980 | Weiner | 606/211 X |
| 5,151,102 | 9/1992 | Kamiyama | 606/52 X |

*Primary Examiner*—Peter A. Aschenbrenner
*Attorney, Agent, or Firm*—Waters & Morse

[57] ABSTRACT

Forceps used in handling laboratory tissue samples being embedded in paraffin are prevented from accumulating congealed paraffin by maintaining the temperature of the grasping portions of the forceps above the point at which the paraffin remains liquid. Electrical resistance heaters are attached to the forceps, and these are energized by an appropriate electric circuit.

3 Claims, 1 Drawing Sheet

HEATED FORCEPS

BACKGROUND OF THE INVENTION

Research and testing laboratories routinely receive biopsy tissue samples for analysis. These are usually embedded in a paraffin matrix, which is then cut into extremely thin slices for viewing under a microscope. The embedding process involves immersing the samples in a small container of melted paraffin, which then is allowed to cool and congeal. Great care must be taken to assure that instruments used in handling these samples do not accumulate congealed paraffin, which has cooled at room temperature after the instrument was dipped in the molten material. This could easily result in entrapment of a piece of a sample, and a transfer of sample material from one piece to another. The validity of the analysis of the sample could thus be compromised.

Handling these samples is normally performed with a forceps (or tweezers). To assure that congealed paraffin does not accumulate on the grasping portion of these instruments, it has become standard practice to repeatedly either dip them in a bath at elevated temperature, or expose them to an open flame. The flame is frowned upon in laboratories as a safety risk, but the necessity to keep the congealed paraffin from forming on the instruments results in relaxing the precautions. Any system for periodically exposing the instruments to a heat source interferes with the embedding operation, and increases the cost accordingly.

SUMMARY OF THE INVENTION

The present invention provides a method and equipment for maintaining the temperature of the handling instruments without repeatedly withdrawing them from use to expose them to a heat source. Conventional forceps are modified to include electrical resistance heaters at the grasping portions, and these heaters can be selected in conjunction with an electrical circuit to maintain the grasping portions at a temperature above the point of liquefaction of the paraffin being used. The circuit elements preferably provide adjustability to select a desired temperature in view of the blend of paraffin being used and the surrounding room conditions. The hands of the user are protected by insulating material surrounding the heaters and the arms of the forceps.

DESCRIPTION OF THE PREFERRED EMBODIMENT

Figure 1:
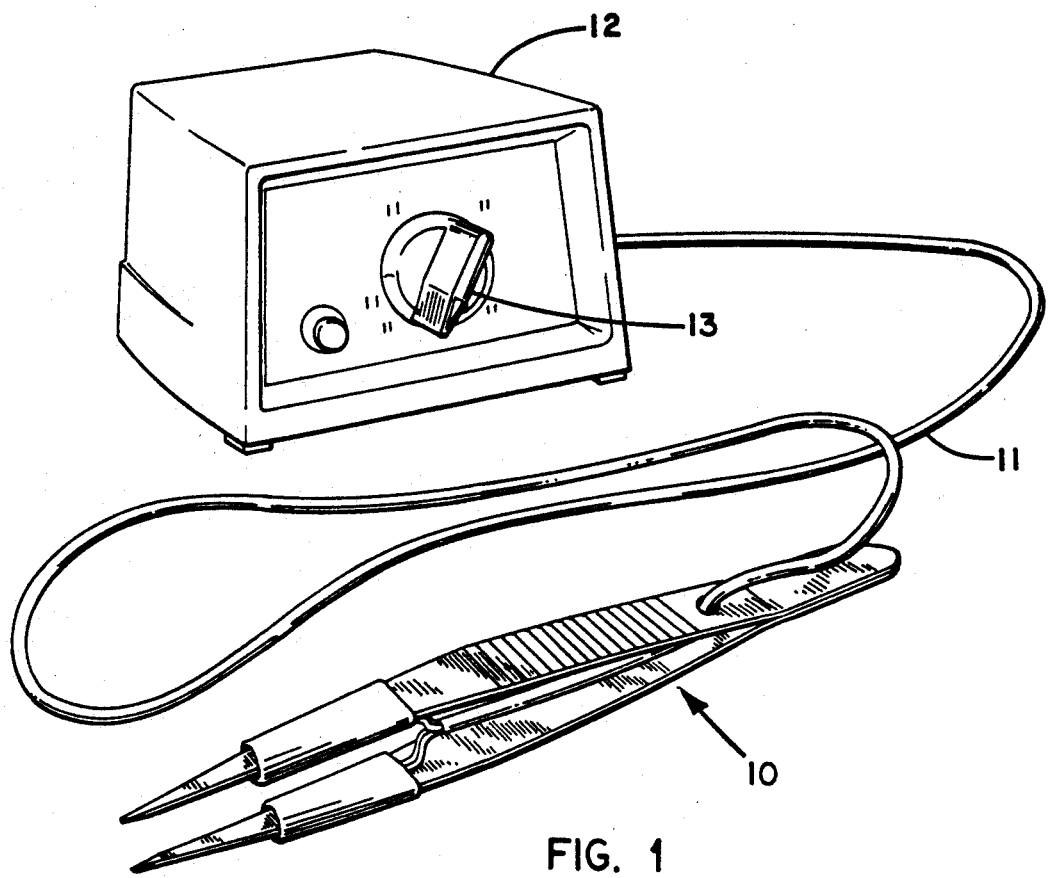
FIG. 1 is a perspective view showing the specially equipped forceps and the associated electrical circuitry.
Figure 2:
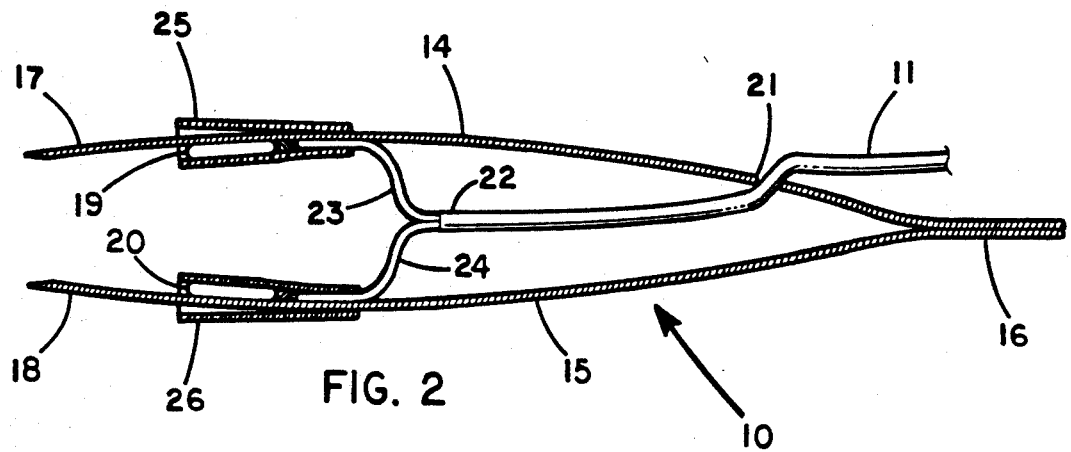
FIG. 2 is a sectional elevation on an enlarged scale showing the arrangement of the components of the system.

The specially equipped tweezers generally indicated at 10 is connected by a four-wire cable 11 to a conventional transformer 12. This is adjustable by positioning the knob 13 to deliver a selected voltage to the heating elements mounted on the forceps 10. Referring to FIG. 2, the tweezers unit is based upon a standard instrument having the spring steel arms 14 and 15 secured together at the end 16 so that the grasping portions 17 and 18 are biased apart to a convenient distance. Small resistors 19 and 20 of approximately 26 ohms resistance are bonded to the arms 14 and 15. The lead cable is led through an opening 21 in the arm 14, and the outer insulation is terminated at 22 to expose the individually insulated pairs of wires 23 and 24, which feed the resistors 19 and 20, respectively. The insulation around the wires 23 and 24 are appropriately stripped clear of insulation at the point of connection to the resistors, and the pieces of insulating tubing 25 and 26 are slipped over the arms 14 and 15 to surround the resistors and the points of connection of the wires.

With the usual paraffin being used, the resistors will each consume approximately 0.4 amperes, and will generate a temperature at the grasping portions of between 58 and 65 degrees centigrade. The paraffin being used is selected according to its melting point for the particular samples that are to be embedded, and with regard to the desired physical conditions of the congealed material. The melting point can thus vary within a range of 52 to 80 degrees centigrade. It is preferable to maintain the grasping portions of the forceps at 2 to 4 degrees over the melting point of the particular paraffin, which is controlled by the adjustment of the knob 13. Freedom from the necessity of withdrawing the tweezers from use in order to apply heat to the grasping portions can easily save half of the usual embedding time, as well as maintain a much higher quality standard in the process.

I claim:

1. A method of handling laboratory samples during the process of embedding said samples in a heat-liquefiable matrix that is normally solid at room temperature, comprising:
    continuously applying heat to at least the tips of forceps to maintain the temperature thereof in excess of the liquefying temperature of said matrix; and
    handling said samples with said forceps to transfer the same to embedding molds containing said matrix.

2. A method as defined in claim 1, wherein said heat is applied by at least one resistor energized by an electrical wire engaging said forceps.

3. A method as defined in claim 2, wherein a said resistor is mounted on both tips of said forceps.

* * * * *